United States Patent [19]

Ondetti et al.

[11] 4,311,705
[45] Jan. 19, 1982

[54] CARBOXYALKANOYL AND HYDROXYCARBAMOYLALKANOYL DERIVATIVES OF SUBSTITUTED PROLINES

[75] Inventors: Miguel A. Ondetti, Princeton; Michael E. Condon, Lawrenceville, both of N.J.

[73] Assignee: E. R. Squibb & Sons, Inc., Princeton, N.J.

[21] Appl. No.: 194,095

[22] Filed: Oct. 6, 1980

[51] Int. Cl.³ .................. C07D 405/04; C07D 409/02; A61K 31/40
[52] U.S. Cl. .............................. 424/274; 260/326.35; 260/326.36; 260/326.43
[58] Field of Search ...................... 260/326.43, 326.35, 260/326.36; 424/274

[56] References Cited

U.S. PATENT DOCUMENTS

| | | | |
|---|---|---|---|
| 4,052,511 | 10/1977 | Cushman et al. | 260/326.43 |
| 4,105,776 | 8/1978 | Ondetti et al. | 260/326.2 |
| 4,154,935 | 5/1979 | Ondetti et al. | 260/326.2 |
| 4,217,359 | 8/1980 | Krapchu | 260/326.2 |

FOREIGN PATENT DOCUMENTS

| | | | |
|---|---|---|---|
| 55-2027025 | 2/1980 | Japan | 260/326.2 |
| 2028327 | 3/1980 | United Kingdom | 260/326.2 |
| 2039478 | 8/1980 | United Kingdom | 260/326.2 |

*Primary Examiner*—Henry R. Jiles
*Assistant Examiner*—Jane T. Fan
*Attorney, Agent, or Firm*—Lawrence S. Levinson; Stephen B. Davis

[57] ABSTRACT

Compounds, compositions and method of alleviating hypertension using a compound of the formula

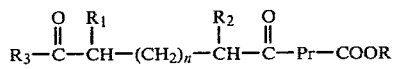

wherein R is hydrogen or lower alkyl;
$R_1$ is hydrogen, lower alkyl or phenyl-lower alkyl;
$R_2$ is hydrogen, lower alkyl or phenyl lower alkyl or halo substituted lower alkyl;
$R_3$ is hydroxy, —NHOH or lower alkoxy;
Pr—COOR is a substituted proline of the structures

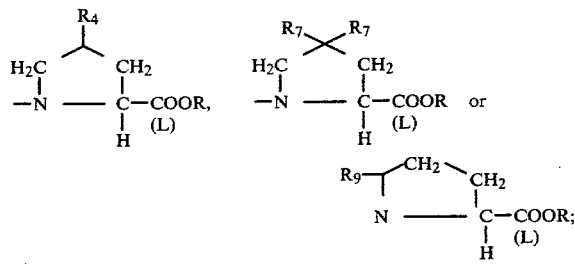

$R_4$ is halogen, keto, azido, cycloalkyl, phenyl, substituted phenyl, phenyl-lower alkyl, substituted phenyl-lower alkyl,

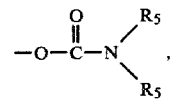

or Y—$R_6$;
$R_5$ is hydrogen or lower alkyl;
Y is oxygen or sulfur;
$R_6$ is lower alkyl, phenyl, substituted phenyl, phenyl-lower alkyl, substituted phenyl-lower alkyl, 1- or 2-naphthyl, substituted 1- or 2- naphthyl, biphenyl, or substituted biphenyl;
$R_7$ is halogen or —Y—$R_8$;
$R_8$ is lower alkyl, phenyl, phenyl-lower alkyl substituted phenyl-lower alkyl, biphenyl, napthyl, or the $R_8$ groups join to complete an unsubstituted 5- or 6-membered ring or such ring wherein one or more carbon atoms are substituted by a lower alkyl or di(lower alkyl) group;
$R_9$ is keto, phenyl, 2- or 4-hydroxyphenyl;
n is 0 or 1; and salts thereof.

13 Claims, No Drawings

CARBOXYALKANOYL AND HYDROXYCARBAMOYLALKANOYL DERIVATIVES OF SUBSTITUTED PROLINES

BACKGROUND OF THE INVENTION

Ondetti et al. in U.S. Pat. No. 4,105,776 discloses compounds of the formula

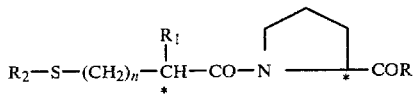

including those wherein the proline ring is substituted with a hydroxy or lower alkyl group as useful in reducing or relieving angiotensin related hypertension.

Cushman et al. in U.S. Pat. No. 4,052,511 discloses compounds of the formula

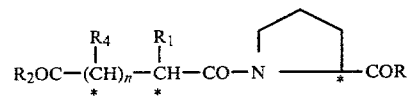

including those wherein the proline ring is substituted with a hydroxy or lower alkyl group as being useful as angiotensin converting enzyme inhibitors.

Ondetti et al. in U.S. Pat. No. 4,154,935 discloses compounds of the formula

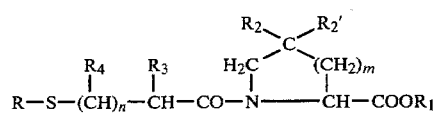

wherein $R_2$ and $R_2'$ are halogen or hydrogen as being useful as hypotensive agents.

Iwao et al. in U.K. Patent Application, GB 2027025 A published Feb. 13, 1980 disclose antihypertensive agents of the formula

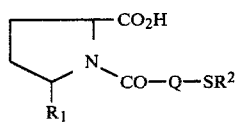

wherein $R_1$ is phenyl or hydroxy substituted phenyl.

Ondetti et al. in U.K. Patent Application GB 2028327 A published Mar. 5, 1980 disclose hypotensive agents of the general formula

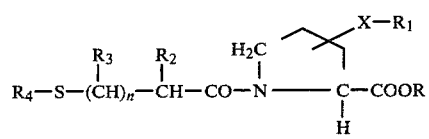

wherein X is oxygen or sulfur and $R_1$ is lower alkyl, phenyl, or phenyl-lower alkyl.

Krapcho in U.S. Pat. No. 4,217,359 discloses compounds of the formula

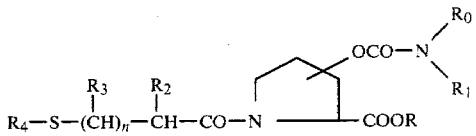

wherein $R_0$ and $R_1$ can be hydrogen or lower alkyl.

Krapcho in U.K. Patent Application GB 2,039,478 A and U.S. Ser. No. 99,164 disclose mercaptoacyl derivatives of proline wherein the proline ring has a diether; dithioether, ketal or thioketal substituent in the 4-position.

SUMMARY OF THE INVENTION

The invention relates to new compounds which have the general formula

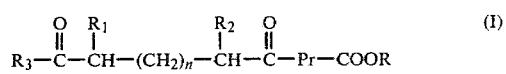

wherein R is hydrogen or lower alkyl.

$R_1$ is hydrogen, lower alkyl or phenyl-lower alkyl.

$R_2$ is hydrogen, lower alkyl, phenyl-lower alkyl or halo substituted lower alkyl.

$R_3$ is hydroxy, —NHOH or lower alkoxy.

Pr—COOR is a substituted proline of the structures

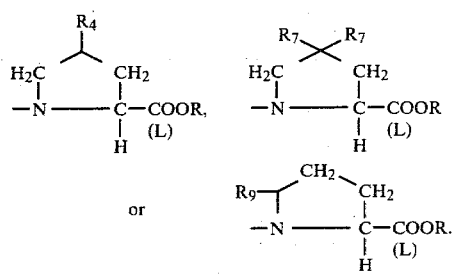

$R_4$ is halogen, keto, azido, cycloalkyl, phenyl, substituted phenyl, phenyl-lower alkyl, substituted phenyl-lower alkyl,

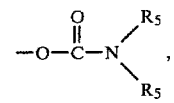

or Y—$R_6$.

$R_5$ is hydrogen or lower alkyl.

Y is oxygen or sulfur.

$R_6$ is lower alkyl, phenyl, substituted phenyl, phenyl-lower alkyl, substituted phenyl-lower alkyl, 1- or 2-naphthyl, substituted 1- or 2-naphthyl, biphenyl, or substituted biphenyl.

$R_7$ is halogen or —Y—$R_8$.

$R_8$ is lower alkyl, phenyl, phenyl-lower alkyl, substituted phenyl-lower alkyl, biphenyl, 1- or 2-naphthyl, substituted 1- or 2-naphthyl, substituted biphenyl or the $R_8$ groups join to complete an unsubstituted 5- or 6-membered ring or such ring wherein one or more carbon atoms are substituted by a lower alkyl or di(lower alkyl) group.

$R_9$ is keto, phenyl, 2- or 4-hydroxyphenyl.

n is 0 or 1 and salts of the formula I compounds.

The L in the above structures indicates a center of asymmetry which is in the L-configuration.

DETAILED DESCRIPTION OF THE INVENTION

The invention in its broadest aspect relates to carboxyalkanoyl (and esters thereof) and hydroxycarbamoylalkanoyl derivatives of proline having formula I above and to salts thereof, to compositions containing such compounds and to the method for using such compounds as anti-hypertensive agents.

The lower alkyl groups represented by any of the variables include straight and branched chain hydrocarbon radicals from methyl to heptyl, for example, methyl, ethyl, propyl, isopropyl, butyl, isobutyl, t-butyl, pentyl, isopentyl and the like. The $C_1$–$C_4$ members and especially the $C_1$ and $C_2$ members, are preferred.

The term lower alkoxy includes such lower alkyl groups bonded through an oxygen and the term lower alkylthio includes such lower alkyl groups bonded through a sulfur.

The halogens are chlorine, bromine and fluorine; chlorine and fluorine being preferred.

The term cycloalkyl refers to saturated rings of 3 to 7 carbon atoms with cyclohexyl being most preferred. The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term phenyl-lower alkyl includes a phenyl ring attached to a lower alkyl group as defined above. Phenylmethyl and phenylethyl are preferred.

The term substituted phenyl and substituted phenyl-lower alkyl include such groups wherein the phenyl ring has a lower alkyl, preferably methyl, lower alkoxy, preferably methoxy, lower alkylthio, preferably methylthio, Cl, Br, F, or hydroxy substituent. When the substituent is methyl, methoxy, Cl or F the phenyl ring may be di or trisubstituted.

The compounds of formula I wherein $R_3$ is lower alkoxy can be prepared by coupling an acid of the formula

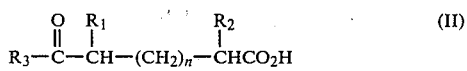

with an imino acid of formula

Pr—COOR       (III)

(wherein Pr—COOR is as defined above, except that it is understood that the ring nitrogen of the free acid is bonded to hydrogen rather than to a carbon chain) by any of the methods known in the art for the preparation of amides. A preferred preparation provides a N-hydroxysuccinimido ester of the acid of formula II which can then be reacted with the imino acid of formula III to give the compound of formula IV:

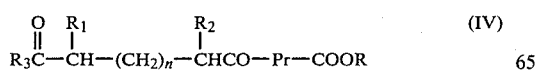

where $R_3$ is lower alkoxy and $R_1$, $R_2$ and Pr—COOR are as defined above.

The compounds of formula I wherein $R_3$ is —NHOH are prepared by reacting a compound of formula V:

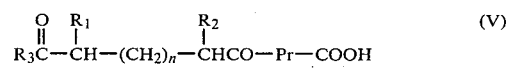

wherein $R_3$ is lower alkoxy with hydroxylamine.

The compounds of formula I wherein $R_3$ is hydroxy are formed by reaction of the formula I compound wherein $R_3$ is alkoxy with NaOH.

Various substituted prolines are disclosed by Mauger et al., Chem. Review, Vol. 66, p 47–86 (1966). Ondetti et al. disclose various alkyl, halogen, ether and thioether substituted prolines in U.S. Pat. Nos. 4,105,776, 4,154,935 and U.K. Application 2,028,327. Iwao et al. in U.K. Application 2,027,025 disclose various 5-substituted prolines.

As disclosed by Krapcho in U.S. Pat. No. 4,217,359, the carbamoyloxy substituted prolines can be obtained by reacting the hydroxy substituted N-protected proline with phosgene and then the amine $HN(R_5)_2$. $R_5$ is as defined above. Removal of the N-protecting group yields the desired starting material.

As disclosed by Krapcho in U.S. Ser. No. 99,164, the prolines of the formula

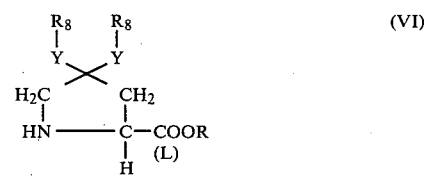

(wherein R and $R_8$ are as defined above) can be prepared by reacting the keto compound of the formula

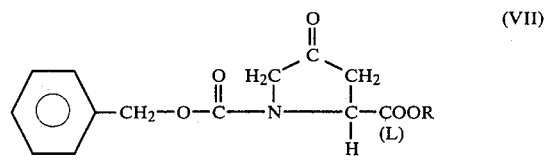

(wherein R is as defined above) with an alcohol or thiol having the formula $R_8$—Y—H       (VIII)

(wherein $R_8$ and Y are as defined above) in the presence of an orthoformate or thioformate of the formula HC(Y—$R_8$)$_3$ and an acid such as concentrated sulfuric acid or p-toluenesulfonic acid. Removal of the carbobenzyloxy group by catalytic hydrogenation when Y is oxygen or by treatment with HBr and acetic acid when Y is sulfur yields the desired starting material. The spiro substituted prolines can be prepared in a similar manner by reacting the keto compound of formula VII with the alcohol or thio of the formula

wherein t is 2 or 3 and $R_{12}$ and $R_{13}$ are independently selected from hydrogen and lower alkyl. This reaction is performed in the presence of p-toluenesulfonic acid and removal of the carbobenzyloxy group yields the desired starting material. When either or both $R_{12}$ and $R_{13}$ are lower alkyl it is preferred that the substituted proline of formula VI be treated directly with a molar excess of the alcohol or thiol of formula IX.

As disclosed by Krapcho in U.S. Ser. No. 164,985 filed July 1, 1980 the 4-substituted proline starting materials wherein the substituent $R_4$ is cycloalkyl, phenyl, substituted phenyl, phenyl-lower alkyl, or substituted phenyl-lower alkyl can be prepared by reacting the 4-keto proline of formula VII with a solution of the Grignard or lithium reagent

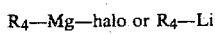

$$R_4-Mg-halo \text{ or } R_4-Li \qquad (X)$$

wherein halo is Br or Cl, to yield

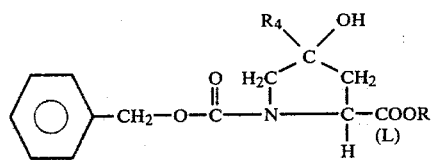

This compound is treated with a dehydrating agent such as p-toluenesulfonic acid, sulfuric acid, potassium bisulfate, or trifluoroacetic acid to yield the 3,4-dehydro-4-substituted proline of the formula

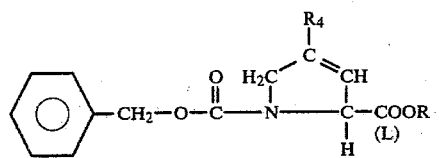

Removal of the N-benzyloxycarbonyl protecting group and hydrogenation of the compound of formula XII yields the desired starting materials. The substituted proline wherein $R_4$ is cyclohexyl can be prepared by further hydrogenation of the 4-phenyl proline compound.

Preferred compounds of this invention with respect to the proline portion of the structure of formula I are those wherein:

$R_4$ is cyclohexyl,

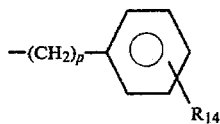

or $Y-R_6$;
when Y is oxygen and
$R_6$ is lower alkyl of 1 to 4 carbons,

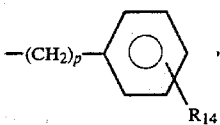

a substituted or unsubstituted 1- or 2-naphthyl of the formula

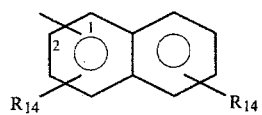

or a substituted or unsubstituted biphenyl of the formula

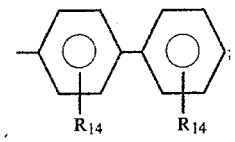

when y is sulfur and $R_6$ is phenyl or substituted phenyl;
p is zero, one or two;
$R_{14}$ is hydrogen, methyl, methoxy, methylthio, Cl, F, Br, or hydroxy;
$R_7$ is Cl, F, or $-Y-R_8$;
$R_8$ is lower alkyl of 1 to 4 carbons or the $R_8$ groups join to complete an unsubstituted 5- or 6-membered ring or said ring in which one or more of the carbons has a methyl or dimethyl substituent;
$R_9$ is phenyl, 2- or 4-hydroxyphenyl.

Preferred carboxyalkanoyl (and esters thereof) and hydroxycarbamoylalkanoyl sidechain portions of the structure of formula I are those wherein:
$R_2$ is methyl, $R_1$ is hydrogen and n is one.
$R_2$ is methyl, n is one, $R_1$ is phenylethyl.

The products of formula I wherein the proline ring is monosubstituted give rise to cis-trans isomerism. The configuration of the final product will depend upon the configuration of the $R_4$ and $R_9$ substituent in the starting material of formula III. In general, it is preferred that the $R_4$ and $R_9$ substituents be in the cis configuration.

The compounds of this invention form basic salts with a variety of inorganic or organic bases. The salt forming ion derived from such bases can be metal ions, e.g., aluminum, alkali metal ions, such as sodium or potassium, alkaline earth metal ions such as calcium or magnesium, or an amine salt ion, of which a number are known for this purpose, for example, ammonium salts, aralkylamines like, dibenzylamine, N,N-dibenzylethylenediamine, lower alkylamines like methylamine, t-butylamine, procaine, lower alkylpiperidines like N-ethylpiperidine, cycloalkylamines, like cyclohexylamine or dicyclohexylamine, 1-adamantane, benzathine, or salts derived from amino acids like arginine, lysine or the like. The physiologically acceptable salts like the sodium or potassium salts can be used medicinally as described below and are preferred. These and other salts which are not necessarily physiologically acceptable are useful in isolating or purifying a product acceptable for the purposes described below, as illustrated with the dicyclohexylamine salt in the examples. The salts are produced by reacting the acid form of the compound with an equivalent of the base supplying the desired basic ion in a medium in which the salt precipitates or in aqueous medium and then lyophilizing. The free acid form can be obtained from the salt by conventional neutralization techniques, e.g., with potassium bisulfate, hydrochloric acid, etc.

The compounds of formula I including their pharmaceutically acceptable salts are useful as hypotensive agents. They inhibit the conversion of the decapeptide angiotensin I to angiotensin II and, therefore, are useful in relieving angiotensin related hypertension. The action of the enzyme renin on angiotensin, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the angiotensinogen→(renin)→angiotensin I→(ACE)→angiotensin II sequence by inhibiting angiotensin converting enzyme and reducing or eliminating the formation of the pressor substance angiotensin II. Thus by the administration of a composition containing one, or a combination of compounds, of formula I angiotensin dependent hypertension in the species of mammal suffering therefrom is alleviated. A single dose, or preferably two to four divided daily doses, provided on a basis of about 0.1 to 100 mg per kilogram of body weight per day, preferably about 1 to 15 mg per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises (for a 70 kg mammal) a total daily dosage of about 30 to 600 mg, preferably about 30 to 300 mg, of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g. chlorthiazide, hydrochlorothiazide, flumethiazide, hydroglumethiazide, bendroflumethiazide, methclothiazide, trichlorothiazide, polythiazide or benthiazide, as well as ethacrynic acid, ticrynafen, chlorthalidone, furosemide, musolimine, bumetanide, triamterene, amiloride and spironolactone, and salts of such compounds.

The compounds of formula I can be formulated for use in the reduction of blood pressure in compositions such as tablets, capsules or elixirs for oral administration or in sterile solutions or suspensions for parenteral administration. About 10 to 500 mg of a compound of mixture of compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrated process details are set forth in the following examples for the various reactions. These examples are preferred embodiments and also serve as models for the preparation of other compounds of this invention. The temperatures are given in degrees on the centigrade scale.

EXAMPLE 1

1-(3-Methoxycarbonyl-R-2-methylpropanoyl)-4,4-ethylene-dioxy-L-proline (a) 3-Methoxycarbonyl-2-methylpropionic acid hydroxysuccinimido ester A mixture of 3-methoxycarbonyl-2-methylpropanoic acid (14.6 g, 100 mmol) and N-hydroxysuccinimide (11.5 g, 100 mmol) in 200 ml 1,2-dimethoxyethane is cooled in an ice bath while stirring under argon. N,N'-Dicyclohexylcarbodiimide (22.2 g, 110 mmol) is added in several portions over a period of five minutes. The mixture is stirred cold for one hour and then at room temperature for two hours. The urea is removed by filtration and the filtrate is taken to dryness in vacuo leaving an oil and a small amount of solid. The oil is dissolved in a mixture of ether-ethyl acetate and filtered through Celite. Removal of the solvent gives 26.2 g yellow oil. This is chromatographed on 600 g Baker silica gel (the sample is preabsorbed from ethyl acetate). After elution of some fast moving material with ether-petroleum ether the desired N-hydroxysuccinimide (O-Su) ester is eluted with ether-petroleum ether 3:1 to give 14.8 g (61%) of 3-methoxycarbonyl-2-methylpropionic acid hydroxysuccinimido ester. A small sample was obtained crystalline on trituration with cold ether, m.p. (s.45°) 52°–57°.

Anal. Calc'd. for $C_{10}H_{13}O_6N$: C, 49.38; H, 5.39; N, 5.76. Found: C, 49.37; H, 5.18; N, 5.70.

(b) 1-(3-Methoxycarbonyl-R-2-methylpropanoyl)-4,4-ethylenedioxy-L-proline

A mixture of 4,4-ethylenedioxy-L-proline (10.4 g, 60 mmol) [prepared as in Example 1A below] 2-methylbutanedioic acid, 1-(2,5-dioxo-1-pyrrolidinyl)4-methyl ester (14.6 g, 60 mmol), triethylamine (16.8 ml, 12.1 g, 120 mmol) and 200 ml of dimethylformamide (DMF) are stirred under argon at room temperature for forty-two hours. The DMF is then removed in vacuo. The residue is dissolved in water and acidified with 10% $KHSO_4$ solution. Sodium chloride is added and the product is extracted into ethyl acetate (4 extractions). The combined extracts are washed once with saturated NaCl solution, dried over $MgSO_4$ and freed of solvent in vacuo leaving 19.6 g of a mixture of oil and solid. This is triturated with ethyl acetate to give 5.0 g (28%) of white solid m.p. (s. 145°) 153°–162°, $[\alpha]_D = 60.8°$ (c=1.26%, $CHCl_3$). Recrystallization of 1.5 g from 30 ml ethyl acetate gives 1-(3-methoxycarbonyl-R-2-methylpropanoyl)-4,4-ethylenedioxy-L-proline 1.15 g, m.p. 164°–167°, $[\alpha]_D = -63°$ (c=1.03%, $CHCl_3$).

Anal. Calc'd. for $C_{13}H_{19}O_7N$: C, 51.82; H, 6.36; N, 4.65. Found: C, 51.94; H, 6.49; N, 4.49

In this and the following examples "s." is used as the abbreviation for sintering and "m.p." is used as the abbreviation for melting point.

EXAMPLE 1A 4,4-Ethylenedioxy-L-proline (a) N-Carbobenzyloxy-4-hydroxy-L-proline 26.5 g (0.20 mole) of 4-hydroxy-L-proline and 32.8 ml. (0.23 mole) of benzyl chloroformate are reacted in 200 ml. of water and 100 ml of acetone in the presence of 20 g (0.02 mole) of potassium bicarbonate and 69.2 g (0.50 mole) of potassium carbonate and worked up with 90 ml of concentrated hydrochloric acid as described in Can. J. Biochem. & Physiol. 37, 584 (1959) to obtain N-carbobenzyloxy-4-hydroxy-L-proline. This product is reacted with cyclohexylamine to form the cyclohexylamine salt yield 69 g, m.p. 193°-195°. The salt (34 g) is neutralized with N-hydrochloric acid to obtain 27 g of free acid as a colorless glass $[\alpha]_D^{26} - 70°$, (c, 1% in chloroform).

(b) N-carbobenzyloxy-4-keto-L-proline 21.5 g (0.81 mole) of N-carbobenzyloxy-4-hydroxy-L-proline is oxidized in 1.2 liters of acetone with 83 ml of 8 N chromic acid in sulfuric acid as described in J.A.C.S. 79, 189 (1957). In order to facilitate the subsequent filtration of chromium salts, 30 g of Celite (diatomaceous earth) is added to the acetone solution before introduction of the oxidizing agent. An air stirrer is employed. The reaction mixture is filtered and the acetone filtrate is concentrated to approximately 300 ml before diluting with 1 liter of chloroform. The solution is washed with 300 ml of saturated sodium chloride (four times), dried (MgSO₄), filtered and the solvent evaporated to give N-carbobenzyloxy-4-keto-L-proline (22.8 g) which is crystallized from ether (50 ml)-hexane (150 ml) to obtain 17.2 g (81%) of product, m.p. 99°-101°, $[\alpha]_D^{26} + 17°$ (c, 1% in chloroform).

(c) N-Carbobenzyloxy-4,4-ethylenedioxy-L-proline

A stirred mixture of 12.8 g (0.049 mole) of N-carbobenzyloxy-4-keto-L-proline, 53 ml (0.095 mole) of ethylene glycol, and 0.35 g of p-toluenesulfonic acid H₂O in 1.31 l. of benzene is heated and the resulting solution is refluxed for 7 hours (water formed is collected in a Dean-Stark apparatus). After standing overnight at room temperature, the lower glycol layer is separated and the benzene solution is washed with 150 ml of saturated sodium chloride, dried (MgSO₄), and the solvent evaporated to give 14.6 g of N-carbobenzyloxy-4,4-ethylenedioxy-L-proline as a syrupy residue. The latter is dissolved in 60 ml of ethanol, filtered, treated with 5 g of cyclohexylamine, and diluted with ether. On seeding and rubbing, the crystalline cyclohexylamine salt separates; weight after cooling overnight, 9.0 g., m.p. 179°-180° (s. 173°). The material is recrystalized from acetonitrile, m.p. 182°-184° (s. 179°), $[\alpha]_D^{26} - 21°$ (c, 1% in EtOh).

The cyclohexylamine salt (8.4 g) is suspended in 40 ml of ethyl acetate, stirred, cooled, and treated with 40 ml of 1 N hydrochloric acid. The layers are separated, the aqueous phase extracted with additional ethyl acetate (3×40 ml), the combined organic layers are dried (MgSO₄), and the solvent evaporated, finally at 0.2 mm. The syrupy residue which begins to crystallize is rubbed under ether and the ether evaporated to give 6.4 g (42%) of nearly colorless N-carbobenzyloxy-4,4-ethylenedioxy-L-proline, m.p. 101°-103° (s. 98°), $[\alpha]_D^{26} - 34°$ (c, 1% in CHCl₃).

(d) 4,4-Ethylenedioxy-L-proline

A solution of 3.2 g (0.0104 mole) of N-carbobenzyloxy-4,4-ethylenedioxy-L-proline in 100 ml of methanol-water (2:1) is treated with 1 g of 5% palladium-carbon and shaken on the Parr hydrogenator for 6 hours. The catalyst is filtered off under nitrogen, washed with methanol, and the combined filtrates evaporated, finally at 0.1-0.2 mm, to give 1.7 g (94%) of colorless solid, 4,4-ethylenedioxy-L-proline; m.p. 245°-247° (dec.); $[\alpha]_D^{26} - 32°$ (c, 0.5% in 1:1 meO-H—H₂O).

EXAMPLE 2

1-(3-Carboxy-R-2-methylpropanoyl)-4,4-ethylenedioxy-L-proline 1-(3-methoxycarbonyl-R-2-methylpropanoyl)-4,4-ethylenedioxy-L-proline (3.0 g, 10 mmol) obtained as in Example 1 is added to 25 ml cold 1 N NaOH. After stirring cold for three hours the solution is acidified with solid KHSO₄. Six ethyl acetate extractions give 2.75 g of white solid. This is triturated with ethyl acetate-ether and 2.4 g (83%) of crystalline material is harvested by filtration. Recrystallization from ethyl acetate (150 ml) gives 1-(3-carboxy-R-2-methylpropanoyl)-4,4-ethylenedioxy-L-proline, 1.9 g, m.p. 155°-158°, $[\alpha]_D = -26.4$ (c=1.36%, absolute ethanol (EtOH).

Anal. Calc'd. for C₁₂H₁₇O₇N: C, 50.17; H, 5.96; N, 4.88. Found: C, 50.39; H, 5.89; N, 4.66.

EXAMPLE 3

1-(3-Carboxy-2-methylpropanoyl)-4,4-ethylene dithio-L-proline R/S: 92.5/7.5.

(a)
1-(3-Methoxycarbonyl-2-methylpropanoyl)-4,4-ethylenedithio-L-proline

A mixture of 4,4-ethylenedithio-L-proline, hydrobromide (11.2 g, 39 mmol) [made as in Example 3A] 3-methoxycarbonyl-2-methylpropionic acid hydroxysuccinimido ester [9.5 g, 29 mmol] made as in Example 1(a) above, and triethylamine (16.4 ml, 117 mmol) in 200 ml dimethylformamide (DMF) is stirred under argon at room temperature for eighteen hours. The dimethylformamide (DMF) is removed in vacuo. The residue is dissolved in water and acidified with 10% KHSO₄ solution. Four extractions with ethyl acetate give a brown oil. This is chromatographed on 600 g Baker silica gel using 0.5% methanol in CHCl₃ and 1% methanol in CHCl₃ to elute the product. A total of 11.1 g (85%) of material is obtained in several pools of fractions. The material appearing the cleanest by TLC weighed 3.5 g. On standing under ether crystalline material is deposited (1.6 g). Saponification of a small sample of this material followed by acid hydrolysis and ion exchange chromatography gives α-methylsuccinic acid which is largely (>85%) the R isomer.

Recrystallization of a small amount of this material gave an analytical sample of 1-(3-methoxycarbonyl-2-methylpropanoyl)-4,4-ethylenedithio-L-proline. M.P. 130°-132°, $[\alpha]_D = -9°$ (c=1.0, absolute ethanol).

Anal. Calc'd. for C₁₃H₁₉O₅NS₃: C, 46.83; H, 5.74; N, 4.20; S, 19.23. Found: C, 46.90; H, 5.90; N, 4.09; S, 19.43.

(b)
1-(3-Carboxy-2-methylpropanoyl)-4,4-ethylenedithio-L-proline

The 1-(3-methoxycarbonyl-2-methylpropanoyl)-4,4-ethylenedithio-L-proline of part (a) (Example 3) 2.6 g, 7.8 mmol) is added to 20 ml cold 1 N NaOH. After stirring in an ice bath for three hours the solution is acidified with solid KHSO₄ and through extraction with ethyl acetate gives 2.7 g solid foam which fails to crystallize $[\alpha]_D = -10.6°$ (c=1.27, absolute ethanol). A small sample of this foam (100 mg) is hydrolyzed at reflux for two hours with 2 ml 1 N HCl. After removal of the solvent in vacuo the residue is dissolved in water and run through a column packed with 10 ml Dowex 50WX2 (H+) resin to give α-methylsuccinic acid $[α]_D = +11.7$ (c=1.05, absolute ethanol) (literature rotation R isomer +15.5; S isomer −15.0). This sample is, therefore, ~85% R isomer.

The foam described above (2.25 g, 7.05 mmol) is dissolved in ethyl acetate (50 ml) and filtered to remove a small amount of insoluble material. To the filtrate is added cyclohexylamine (1.7 ml, 1.485 g, 15 mmol). The white solid that precipitated is harvested and recrystallized from isopropanol to give 1.7 g (47%) 1-(3-carboxy-2-methylpropanoyl)-4,4-ethylenedithio-L-proline m.p. (180°) 190°-192°, $[α]_D = -15.4°$ (c=0.975, absolute ethanol).

Anal. Calc'd. for $C_{12}H_{17}O_5NS_2 \cdot 2\ C_6H_{13}N$: C, 55.68; H, 8.37; N, 8.12; S, 12.39. Found: C, 55.47; H, 8.47; H, 8.46; S, 12.65.

The cyclohexylamine salt (1.7 g, 3.3 mmol) is dissolved in 10% $KHSO_4$ solution and the diacid is extracted into ethyl acetate, dried and freed of solvent in vacuo to give 1.0 g (95%) of white solid foam. $[α]_D = -10.2°$ (c=1.26, absolute ethanol). A small sample of this material is hydrolyzed as described above to give the α-methylsuccinic acid. $[α]_D = +13.2°$ (c=1.13, absolute ethanol). Therefore, this sample is about 92.5% R isomer.

EXAMPLE 3A 4,4-Ethylenedithio-L-proline hydrobromide (a) N-Carbobenzyloxy-4,4-ethylenedithio-L-proline, methyl ester A stirred solution of 3.9 g (0.014 mole) of N-carbobenzyloxy-4-keto-L-proline, methyl ester in 60 ml of methylene chloride is treated with 3 ml (0.036 mole) of ethanedithiol, cooled to 8°, and treated under an argon blanket with 3 ml (0.024 mole) of boron trifluoride etherate. After removing the cooling bath, the pale yellow solution is stirred for an additional hour and kept overnight at room temperature. The solution is stirred, treated with several pieces of crushed ice, followed by 20 ml of water. After 30 minutes the layers are separated and the aqueous phase (50 ml) is extracted with additional methylene chloride (3×30 ml). The combined organic layers are washed with 50 ml of saturated sodium chloride solution, dried ($MgSO_4$), and the solvent removed on a rotary evaporator to give 6 g (100%) of a pale yellow oil N-carbobenzyloxy-4,4-ethylenedithio-L-proline, methyl ester.

(b) N-Carbobenzyloxy-4,4-ethylenedithio-L-proline

The methyl ester product from part (a) (7.4 g, approximately 0.018 mole) is dissolved in 65 ml of methanol, treated dropwise at −1° to 4° with 14.5 ml (0.029 mole) of 2 N sodium hydroxide, kept at 0° for one hour, and at room temperature overnight. After removing about half the solvent on a rotary evaporator, the solution is diluted with 125 ml of water, washed with ether (wash discarded), acidified while cooling with 5 ml of 1:1 hydrochloric acid to a pH of 2, and extracted with ethyl acetate (4×50 ml). The combined extracts are washed with 50 ml. of saturated sodium chloride, dried ($MgSO_4$), and the solvent evaporated to give 6 g of a pale yellow viscous oil. This oil is dissolved in 25 ml of ethanol, treated with 1.8 g of cyclohexylamine in 5 ml of ethanol, and diluted to 300 ml with ether. On seeding and rubbing, the crystalline cyclohexylamine salt separates to yield after overnight cooling 5.7 g of N-carbobenzyloxy-4,4-ethylenedithio-L-proline cyclohexylamine salt; m.p. 205°-207° (s. 201°). Recrystallization from 50 ml of ethanol-400 ml ether yields 4.9 g of colorless solid salt; m.p. 207°-209° (s. 201°), $[α]_D^{25} -15°$ (c, 1% in chloroform).

The cyclohexylamine salt (4.8 g) is suspended in 25 ml of ethyl acetate, stirred, and treated with 25 ml of 1 N hydrochloric acid. When two clear layers are obtained, they are separated, the aqueous phase is extracted with additional ethyl acetate (3×25 ml), the combined organic layers are dried ($MgSO_4$), and the solvent evaporated to give 3.8 g (62%) of N-carbobenzyloxy-4,4-ethylenedithio-L-proline as a pale yellow viscous syrup.

(c) 4,4-Ethylenedithio-L-proline, hydrobromide

N-Carbobenzyloxy-4,4-ethylenedithio-L-proline (3.7 g, 0.011 mole) is treated with 20 ml of hydrogen bromide in acetic acid (30–32%), stoppered loosely, and stirred magnetically. Mixing is difficult due to the viscosity of the starting material and the latter is broken up as much as possible with a spatula. In the meantime, the crystalline product begins to separate. Further quantities of hydrogen bromide in acetic acid are added after 15 minutes (10 ml) and after 25 minutes (5 ml) and stirring is continued for a total of 35 minutes. Ether (250 ml) is added to complete precipitation of the product and after cooling for 15 minutes the cream colored material is filtered under nitrogen, washed with ether, and dried in vacuo to give 2.7 g of 4,4-ethylenedithio-L-proline, hydrobromide; m.p. 240°–242° (dec.); sintering and darkening from approximately 200°; $[α]_D^{26} -40°$ (c, 0.5% in 1:1 chloroform-methanol).

EXAMPLES 4–16

Following the procedure of Examples 1 and 2 wherein the compound of Column I is treated to form the compound of column II which is then treated to form the product compound of Column III.

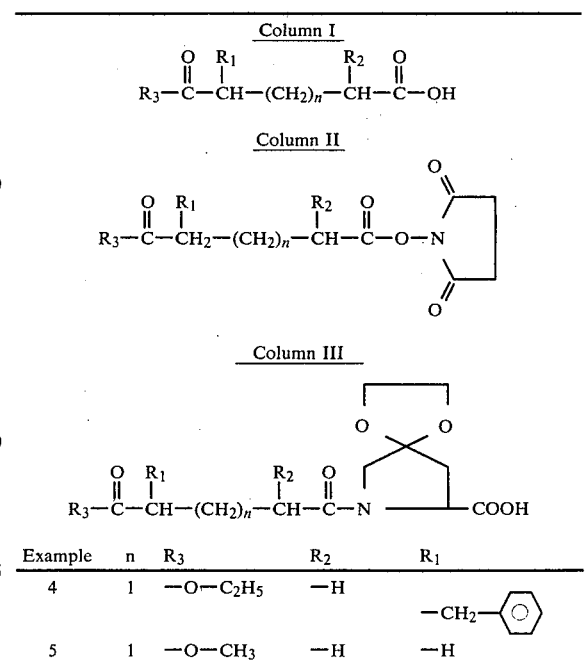

| Example | n | $R_3$ | $R_2$ | $R_1$ |
|---|---|---|---|---|
| 4 | 1 | $-O-C_2H_5$ | $-H$ | $-CH_2-\text{C}_6\text{H}_5$ |
| 5 | 1 | $-O-CH_3$ | $-H$ | $-H$ |

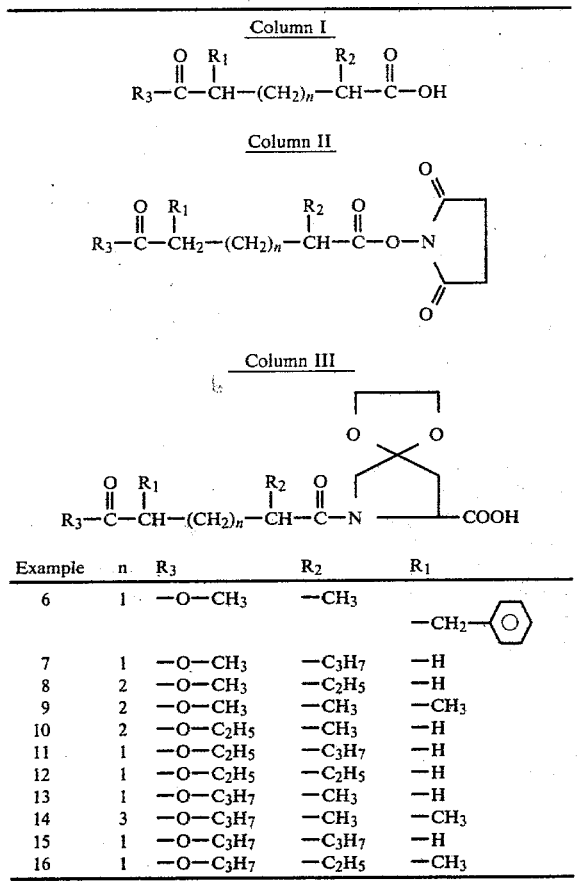

| Example | n | R₃ | R₂ | R₁ |
|---------|---|------|------|------|
| 6 | 1 | —O—CH₃ | —CH₃ | —CH₂—⌬ |
| 7 | 1 | —O—CH₃ | —C₃H₇ | —H |
| 8 | 2 | —O—CH₃ | —C₂H₅ | —H |
| 9 | 2 | —O—CH₃ | —CH₃ | —CH₃ |
| 10 | 2 | —O—C₂H₅ | —CH₃ | —H |
| 11 | 1 | —O—C₂H₅ | —C₃H₇ | —H |
| 12 | 1 | —O—C₂H₅ | —C₂H₅ | —H |
| 13 | 1 | —O—C₃H₇ | —CH₃ | —H |
| 14 | 3 | —O—C₃H₇ | —CH₃ | —CH₃ |
| 15 | 1 | —O—C₃H₇ | —C₃H₇ | —H |
| 16 | 1 | —O—C₃H₇ | —C₂H₅ | —CH₃ |

EXAMPLE 17

1-(3-Carboxylpropanoyl)-4,4-ethylenedithio-L-proline

Following the procedure of Example 3 but substituting 3-methoxycarbonylpropanoic acid hydroxysuccinimido ester for 3-methoxycarbonyl-2-methylpropanoic acid hydroxysuccinimido ester then 1-(3-carboxylpropanoyl)-4,4 ethylenedithio-L-proline is obtained.

EXAMPLE 18

1-(3-Carboxy-2,3-dimethylpropanoyl)-4,4-ethylenedithio-L-proline

Following the procedure of Example 3 but substituting 3-methoxycarbonyl-2,3-dimethylpropanoic acid hydroxysuccinimido ester for 3-methoxycarbonyl-2-methylpropanoic acid hydroxysuccinimido ester then 1-(3-carboxy-2,3-dimethylpropanoyl)-4,4 ethylenedithio-L-proline is formed.

EXAMPLE 19

1-(3-Ethoxycarbonyl-2-methylpropanoyl)-4,4-ethylenedithio-L-proline

Following the procedure of Example 3 but substituting 3-ethoxycarbonyl-2-methylpropanoic acid hydroxysuccinimido ester in place of 3-methoxycarbonyl-2-methylpropanoic acid hydroxysuccinimido ester then 1-(3-ethoxycarbonyl-2-methylpropanoyl)-4,4 ethylenedithio-L-proline is formed.

EXAMPLE 20

1-(3-Hydroxycarbamoyl-2-methylpropanoyl)-4,4-ethylenedithio-L-proline 1-(3-ethoxycarbonyl-2-methylpropanoyl)-4,4-ethylenedithio-L-proline (2.4 g) is dissolved in absolute ethanol (8 ml). An ethanolic solution of hydroxylamine [prepared from hydroxylamine hydrochloride (0.7 g) and sodium ethylate] is added followed by a solution of sodium (0.23 g) in absolute ethanol (8 ml). After two hours the reaction mixture is added to vigorously stirred ether (500 ml). The precipitate is filtered and dried to obtain 1-(3-hydroxycarbamoyl-2-methylpropanoyl)-4,4 ethylenedithio-L-proline, yield 2 g. The free acid is prepared by treatment with an ion exchange resin (Dowex 50 in the hydrogen form).

EXAMPLE 21

4-[(4-Chlorophenyl)methyl]-1-(3-methoxycarbonyl-2-methylpropanoyl-L-proline (a) [(4-Chlorophenyl)methyl]triphenylphosphonium chloride A stirred solution of 158 g, (0.6 mole) of triphenylphosphine in 800 ml of xylene is treated with 97 g of 4-chlorobenzyl chloride. The resulting solution is heated (product begins to crystallize at this point) and refluxed for six hours. After standing overnight at room temperature, the solid is filtered, washed with xylene and then with ethyl acetate, and dried in a desiccator to yield 161 g of colorless solid [(4-chlorophenyl)methyl]-triphenylphosphonium chloride; m.p. 283°–285°.

(b)
N-Carbobenzyloxy-4-[(4-chlorophenyl)methylene]-L-proline

Interaction of 15.2 g (0.32 mole) of 50% sodium hydride (oil dispersion) with 300 ml of dimethylsulfoxide, followed by treatment with a suspension of 135 g (0.32 mole) of [(4-chlorophenyl)methyl]triphenylphosphonium chloride in 300 ml of dimethyl sulfoxide (warmed to 70° and then cooled to 22°) and then with a solution of 26.4 g (0.1 mole) of N-carbobenzyloxy-4-keto-L-proline in 80 ml of dimethylsulfoxide according to the procedure of Example 21A (a) gives 13 g of pale yellow product as a sticky foam. This material is dissolved in 30 ml of acetonitrile and treated with 6.5 g of dicyclohexylamine to yield 15.3 g of nearly colorless N-carbobenzyloxy-4-[(4-chlorophenyl)methylene]-L-proline, dicyclohexylamine salt; m.p. 180°–182° (s. 177°); [α]$_D^{25}$+6.2° (c, 1% in chloroform).

Anal. Cal'd. for C₂₀H₁₈ClNO₄.C₁₂H₂₃N: C, 69.48; H, 7.47; N, 5.07; Cl, 6.41. Found: C, 69.14; H, 7.20; N, 5.03; Cl, 6.23.

The above dicyclohexylamine salt (7.5 g) is suspended in ethyl acetate and treated with 10% potassium bisulfate according to the procedure of Example 21A(a) to give 5.3 g of sticky N-carbobenzyloxy-4-[(4-chlorophenyl)methylene]-L-proline.

(c) cis-4-[(4-Chlorophenyl)methyl]-L-proline, hydrobromide

A solution of 5.3 g (0.014 mole) of N-carbobenzyloxy-4-[(4-chlorophenyl)methylene]-L-proline in 150 ml of ethanol is treated with 0.45 g of platinum dioxide and shaken on a Parr hydrogenator at a starting pressure of 15 lbs. (bottle gauge). The uptake of hydrogen is carefully monitored and whenever the pressure falls to 5 lbs the bottle is replenished with hydrogen to 15 lbs. A noticeable slowing down of the rate of hydrogen uptake is observed after eight minutes and the hydrogenation is interrupted after a total of ten minutes (21.5 lbs of hydrogen). The catalyst is filtered off (celite bed under nitrogen atmosphere), washed well with ethanol, and the combined filtrates are evaporated, finally at 0.2 mm, to yield 4.6 g of N-carbobenzyloxy-cis-4-[(4-chlorophenyl)methyl]-L-proline as a colorless brittle foam.

This material (4.5 g, 0.012 mole) is treated with 25 ml of hydrogen bromide in acetic acid (30–32%), stoppered loosely, and stirred magnetically. After 30 minutes the yellow-orange mixture (some crystalline product separates) is diluted to 500 ml with ether to complete precipitation and stirred with cooling for 30 minutes. The light pink product is filtered under nitrogen, washed with ether, and dried in vacuo to yield 3.3 g of cis-4-[(4-chlorophenyl)methyl]-L-proline, hydrobromide; m.p. 233°–235° (dec., preceded by gradual darkening and sintering); $[\alpha]_D^{25} + 1.5°$; (c, 1% in methanol).

Anal. Calc'd. for $C_{12}H_{14}ClNO_2 \cdot HBr$: C, 44.95; H, 4.72; N, 4.37; Br, 24.92. Found: C, 45.03; H, 4.72; N, 4.38; Br, 24.65.

(d)
4-[(4-Chlorophenyl)methyl]-1-(3-methoxycarbonyl-2-methylpropanoyl)-L-proline Following the procedure of Example 3 but substituting cis-4-[(4-chlorophenyl)methyl]-L-proline hydrobromide from step (c) above, in place of 4,4-ethylenedithio-L-proline hydrobromide then 4-[(4-chlorophenyl)methyl]-1-(3-methoxycarbonyl-2-methylpropanoyl)-L-proline is formed.

EXAMPLE 21A (a) N-Carbobenzyloxy-4-(phenylmethylene)-L-proline

To a 1 liter flask are added 7.6 g (0.16 mole) of sodium hydride (50% suspension) and 150 ml of dry dimethylsulfoxide. The suspension is stirred and then maintained at 70° for thirty minutes (all of the sodium hydride has reacted at this point). The solution is cooled to 30° and treated portionwise with a suspension of 61.1 g (0.16 mole) of benzyltriphenylphosphonium chloride (dried in vacuo overnight) in 150 ml dimethylsulfoxide and the resulting intense red suspension is heated to 70°. This mixture is cooled to 25° and treated with a solution of 13.2 g (0.05 mole) of N-carbobenzyloxy-4-keto-L-proline in 40 ml of dimethylsulfoxide over a period of twenty minutes. This mixture is maintained at 65°–70° for four hours, allowed to stand overnight at room temperature, and then poured onto a solution of 10 g of potassium bicarbonate in 400 ml of icewater. Some ice is added to the mixture to bring the volume to 1 liter and it is then extracted three times with 250 ml portions of ether. The ether phases are discarded and the aqueous phase is cooled and acidified with 50 ml of 6 N hydrochloric acid. The product is extracted with 250 ml of chloroform and then twice with 100 ml of chloroform. The organic phases are combined, dried (MgSO$_4$), filtered and the solvent evaporated to give 102 g of pale brown viscous residue. The latter is triturated with 500 ml of ether. The ether is decanted from the brown residue (mostly triphenylphosphineoxide) and the latter is triturated twice with 100 ml of ether. The ether phases are combined, cooled and treated portionwise with a solution of 10 g of sodium bicarbonate in 200 ml of water. The layers are separated and the organic phase is extracted with 10 ml of water. The ether phase is discarded and the aqueous phases are combined, cooled, acidified with 18 ml of 6 N hydrochloric acid and extracted three times with 100 ml of ether. The organic layers are combined, dried (MgSO$_4$), filtered and the solvent evaporated to give 8.9 g (52.6%) of a pale yellow foam. The bulk of this compound 8.6 g) is dissolved in 20 ml of acetonitrile and treated with 4.6 g of dicyclohexylamine. The product slowly crystallizes. After standing overnight in the cold, the nearly colorless dicyclohexylamine salt is filtered and dried to yield 11.0 g of N-carbobenzyloxy-4-(phenylmethylene)-L-proline, dicyclohexylamine; m.p. 142°–150°. After recrystallization from 65 ml of acetonitrile, 9.5 g of nearly colorless dicyclohexylamine salt are obtained; m.p. 150°–155°; $[\alpha]_D^{25} + 7.7°$ (c, 1% in chloroform).

Anal. Calc'd. for $C_{20}H_{19}NO_4 \cdot C_{12}H_{23}N$: C, 74.09; H, 8.16; N, 5.40. Found: C, 73.87; H, 8.18; N, 5.33.

This dicyclohexylamine salt (9.4 g) is suspended in 100 ml of ethyl acetate and treated with 100 ml of 10% potassium bisulfate. The mixture is shaken and the aqueous phase is extracted twice with 50 ml of ethyl acetate. The organic phases are combined, dried (MgSO$_4$), filtered and the solvent evaporated to give 6.4 g (38%) of pale yellow foam-like solid N-carbobenzyloxy-4-(phenylmethylene)-L-proline; $[\alpha]_D^{25} - 2.5°$ (c, 1% in chloroform); R$_f$ 0.29 (85:15 toluene:acetic acid on silica gel).

Treatment of this material according to the procedures of Example 21 (c) and (d) yields the corresponding 4-(phenylmethyl)-L-proline product.

EXAMPLE 22

1-(3-Methoxycarbonyl-2R-methylpropanoyl)-4-S-phenylthio-L-proline (a) 3-Methoxycarbonyl-2-R-methylpropionic acid (RS)-3-Methoxycarbonyl-2-methylpropionic acid (36.8 g) is dissolved in ether (200 ml) and mixed with dehydroabietylamine (91.3 g) dissolved in 400 ml of ether. After storing the mixture for one hour at room temperature the crystals are filtered and recrystallized from ethyl acetate, to yield 25.2 g of 3-methoxycarbonyl-2-R-methylpropionic acid m.p. (173°) 144°–146° C. $[\alpha]^{22} = +30.5°$ (c=1.5, EtOH).

(b)
1-(3-Methoxycarbonyl-2R-methylpropanoyl)-4-S-phenylthio-L-proline

3-Methoxycarbonyl-2-R-methylpropionic acid (2 g, 13.75 mmoles) and N-hydroxybenzotriazole (1.91 g, 12.5 mmoles) are dissolved in tetrahydrofuran (36 ml) and to this solution, chilled in an ice bath, dicyclohexylcarbodiimide (2.57 g, 12.5 mmoles) is added. After two hours stirring at room temperature the precipitate is filtered off and the filtrate is dissolved in N,N-dimethylformamide, then (36 ml) cis-4-phenylthio-L-proline (3.8 g, 12.5 mmoles) and triethylamine (3.5 ml) are added. The reaction is allowed to proceed for eighteen hours at room temperature, the solvent is removed in vacuo, the residue is dissolved in ethyl acetate and washed with 0.1 N, HCl, saturated aqueous sodium chloride, dried (MgSO$_4$) and concentrated to dryness. The residue is then taken into ethyl acetate, the crystals are filtered off and the filtrate concentrated to dryness and chromatographed on a column of silica gel with benzene:acetic acid (8:2). The fractions containing the desired product are concentrated to dryness, reevaporated from water (freeze-drying) and crystallized from ethyl acetate-hexane to yield 3.3 g of 1-(3-methoxycarbonyl-2-R-methylpropanoyl)-4-S-phenylthio-L-proline m.p. (88°) 94°–96°.

EXAMPLE 23

1-(4-Methoxycarbonyl-2R-methylbutanoyl)-4-S-phenylthio-L-proline (a) 4-Methoxycarbonyl-2-R-methylbutyric acid Substituting 4-methoxycarbonyl-2-methylbutyric acid for 3-R-methoxycarbonyl-2-methylpropionic acid while following the procedure of Example 22(a), then 4-methoxycarbonyl-2R-methylbutyric acid is obtained.

(b)
1-(4-Methoxycarbonyl-2R-methylbutanoyl)-4-S-phenylthio-L-proline

Substituting 4-methoxycarbonyl-2-R-methylbutyric acid for 3-methoxycarbonyl-2-R-methylpropionic acid while following the procedure of Example 22(b), then 1-(4-methoxycarbonyl-2R-methylbutanoyl)-4-S-phenylthio-L-proline is obtained.

EXAMPLE 24

1-((RS)-3-methoxycarbonyl-5-phenyl-2R-methylpentanoyl)-4-S-phenylthio-L-proline (a)
(RS)-3-Methoxycarbonyl-5-phenyl-2R-methylpentanoic acid 3-methoxycarbonyl-2R-methylpropionic acid (46 g, 10 mmoles) is added to a one molar solution of lithium diisopropylamide in tetrahydrofuran (20 ml) chilled at −78°. The enolate is allowed to form for forty minutes at −78°. Phenethylbromide (185 g, 10 mmole) is added and the reaction mixture is allowed to reach 4° C. and maintained at this temperature until the reaction is complete as monitored by tlc. The reaction mixture is diluted with ethyl acetate and washed with 10% aqueous bisulfate and water. The organic layer is dried (MgSO$_4$) and concentrated to dryness to give (RS)-3-methoxycarbonyl-5-phenyl-2R-methylpentanoic acid.

(b)
1-((RS)-3-methoxycarbonyl-5-phenyl-2R-methylpentanoyl)-4-S-phenylthio-L-proline.

Substituting (RS)-3-methoxycarbonyl-5-phenyl-2R-methylpentanoic acid for 3-methoxycarbonyl-2-R-methylpropionic acid while following the procedure of Example 22(b) then 1-((RS)-3-methoxycarbonyl-5-phenyl-2R-methylpentanoyl)-4-S-phenylthio-L-proline is obtained.

EXAMPLE 25

1-(4-Methoxycarbonyl-6-phenyl-2-R-methylhexanoyl)-4-S-phenylthio-L-proline (a) 4-Methoxycarbonyl-6-phenyl-2-R-methylhexanoic acid By substituting 4-methoxycarbonyl-2-R-methylbutyric acid for the 3-methoxycarbonyl-2-R-methylpropionic acid in the procedure of Example 24(a), then 4-methoxycarbonyl-6-phenyl-2-R-methylhexanoic acid is obtained.

(b)
1-(4-Methoxycarbonyl-6-phenyl-2-R-methylhexanoyl)-4-S-phenylthio-L-proline

By substituting 4-methoxycarbonyl-6-phenyl-2-R-methylhexanoic acid for 3-methoxycarbonyl-2-R-methylpropionic acid while following the procedure of Example 22(b) then 1-(4-methoxycarbonyl-6-phenyl-2-R-methylhexanoyl)-4-S-phenylthio-L-proline is obtained.

EXAMPLE 26

1-(4-Ethoxycarbonyl-2-methyloctanoyl)-4-S-phenylthio-L-proline (a) 4-Ethoxycarbonyl-2-methyloctanoic acid benzyl ester 4,4-Diethoxycarbonyl-2-methylbutyric acid benzyl ester [prepared by Michael condensation of benzylmethacrylate and malonic ester as per J. Am. Chem. Soc., 52, 4598 (1930)] (3.36 g, 10 mmole) is added to a solution of 0.23 g of sodium in ethanol (3 ml) chilled to 10° C. Butyl iodide (1.85 g, 10 mmoles) is added and the mixture is refluxed for four hours. The solvent is removed in vacuo and the mixture is distilled in vacuo to yield 4,4-diethoxycarbonyl-2-methyloctanoic acid benzyl ester.

This material (3 mmole) and 1,4-diazabicyclo[2.2.2]octane (30 mmole) are refluxed in O-xylene (45 mmole) for thirty hours. The mixture is fractionated in vacuo to yield 4-ethoxycarbonyl-2-methyloctanoic acid benzyl ester.

(b) 4-Ethoxycarbonyl-2-methyloctanoic acid 4-ethoxycarbonyl-2-methyloctanoic acid benzyl ester (10 g) is dissolved in ethanol (100 ml), 10% palladium on charcoal (2 g) is added, and the mixture is hydrogenated until complete removal of the benzyl ester is achieved to yield 4-ethoxycarbonyl-2-methyloctanoic acid.

(c)
1-(4-ethoxycarbonyl-2-methyloctanoyl)-4-S-phenylthio-L-proline

By substituting 4-ethoxycarbonyl-2-methyloctanoic acid for 3-methoxycarbonyl-2-R-methylpropionic acid while following the procedure of Example 22(b) then 1-(4-ethoxycarbonyl-2-methyloctanoyl)-4-S-phenylthio-L-proline is obtained.

EXAMPLES 27–56

By following the procedure of Example 22 but using a proline of Column I in place of the cis-4-phenylthio-L-proline, of Example 22(b); and using the acid compound of Column II in place of the 3-methoxycarbonyl-2-R-methylpropionic acid of Example 22(b) then the product of Column III is obtained.

Column I
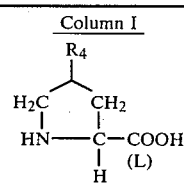
Column II
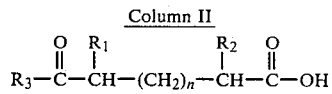
Column III
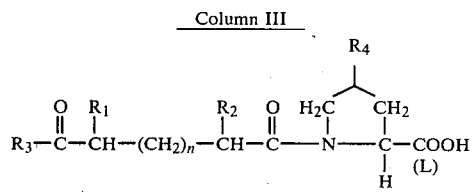
| Example | R₁ | R₂ | R₃ | R₄ | n |
|---------|-----|-----|-----|-----|---|
| 27 | —CH₃ | —H | —OCH₃ | —F | 1 |
| 28 | —CH₂—CH₂—C₆H₅ | —H | —OCH₃ | —Br | 1 |
| 29 | —H | —CH₃ | —OCH₃ | —Br | 1 |
| 30 | —CH₃ | —H | —OCH₃ | —C₆H₅ | 1 |
| 31 | —CH₂—C₆H₅ | —H | —OCH₃ | —Cl | 1 |
| 32 | —CH₂—CH₂—C₆H₅ | —H | —OCH₃ | =O | 1 |
| 33 | —CH₂—CH₂—C₆H₅ | —H | —OCH₃ | —N=N=N | 1 |
| 34 | —H | —H | —OCH₃ | —CH(cyclohexyl) | 1 |
| 35 | —H | —H | —OCH₃ | —C₆H₅ | 1 |
| 36 | —H | —H | —OCH₃ | —C₆H₄—Cl | 1 |
| 37 | —H | —H | —OCH₃ | —CH₂—C₆H₅ | 1 |
| 38 | —H | —H | —OCH₃ | —CH₂—C₆H₄—Cl | 1 |
| 39 | —H | —H | —OCH₃ | —O—C(=O)—NH₂ | 1 |

-continued
Column I
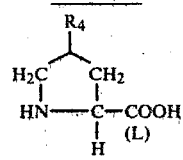
Column II
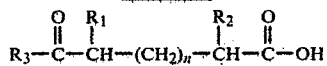
Column III
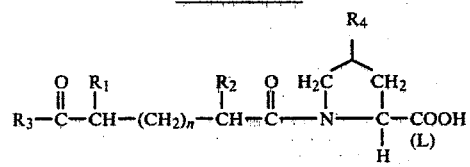
| Example | $R_1$ | $R_2$ | $R_3$ | $R_4$ | n |
|---|---|---|---|---|---|
| 40 | —H | —H | —OCH$_3$ | 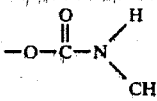 | 1 |
| 41 | —CH$_2$—CH$_2$—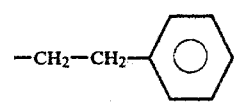 | —H | —OCH$_3$ | —F | 1 |
| 42 | —H | —H | —OCH$_3$ | —OCH$_3$ | 1 |
| 43 | —H | —H | —OCH$_3$ | —SCH$_3$ | 1 |
| 44 | —H | —H | —OCH$_3$ | —O—CH$_2$CH$_2$CH$_3$ | 1 |
| 45 | —H | —H | —OCH$_3$ | —O—C(CH$_3$)$_3$ | 1 |
| 46 | —H | —H | —OCH$_3$ | 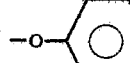 | 1 |
| 47 | —H | —H | —OCH$_3$ |  | 1 |
| 48 | —H | —H | —OCH$_3$ | 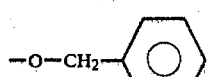 | 1 |
| 49 | —H | —H | —OCH$_3$ |  | 1 |
| 50 | —H | —H | —OCH$_3$ | 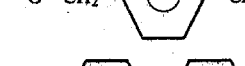 | 1 |
| 50A | —H | —H | —OCH$_3$ |  | 1 |
| 51 | —H | —H | —OCH$_3$ | 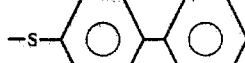 | 1 |
| 51A | —H | —H | —OCH$_3$ | 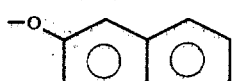 | 1 |
| 52 | —C$_2$H$_5$ | —H | —OCH$_3$ | =O | 1 |

-continued-

Column I

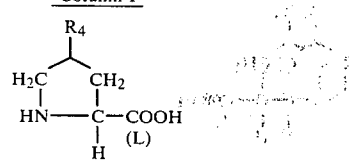

Column II

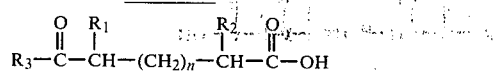

Column III

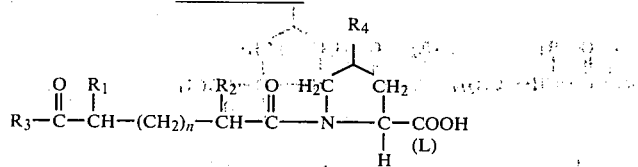

| Example | $R_1$ | $R_2$ | $R_3$ | $R_4$ | n |
|---|---|---|---|---|---|
| 53 | –CH$_2$–CH$_2$–C$_6$H$_5$ | –H | –OCH$_2$CH$_3$ | –Cl | 1 |
| 54 | –CH$_2$–CH$_2$–C$_6$H$_5$ | –CH$_3$ | –OCH$_2$CH$_3$ | –CH$_2$–C$_6$H$_5$ | 1 |
| 55 | –H | –CH$_2$–C$_6$H$_4$–Cl | –OCH$_3$ | –C$_6$H$_5$ | 1 |
| 56 | –H | –CH$_2$–C$_6$H$_5$ | –OCH$_3$ | –C$_6$H$_5$ | 1 |

EXAMPLES 57–69

By following the procedure of Example 22 but using a proline of Column I in place of the cis-4-phenyl-thio-L-proline, of Example 22(b); and using the acid compound of Column II in place of the 3-methoxy-carbonyl-2-R-methylpropionic acid of Example 22(b) then the product of Column III is obtained.

Column I
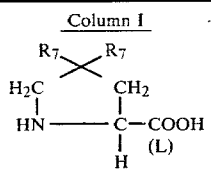
Column II
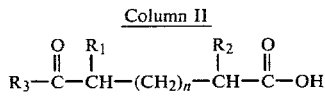
Column III
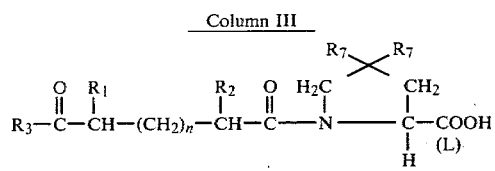
| Example | $R_1$ | $R_2$ | $R_3$ | $R_7$ | n |
|---|---|---|---|---|---|
| 57 | —CH₂—CH₂—C₆H₅ | —H | —OCH₃ | —Cl | 1 |
| 58 | —H | —CH₃ | —OCH₃ | —Cl | 0 |
| 59 | —H | —H | —OCH₃ | —Br | 1 |
| 60 | —H | —H | —OCH₃ | —F | 1 |
| 61 | —H | —H | —OCH₃ | —O—CH₃ | 1 |
| 62 | —H | —H | —OCH₃ | —O—C₆H₅ | 1 |
| 63 | —H | —H | —OCH₃ | —O—CH₂—C₆H₅ | 1 |
| 64 | —H | —H | —OCH₃ | —O—CH₂—C₆H₄—Cl | 1 |
| 65 | —H | —H | —OCH₃ | —O—C₆H₄—C₆H₅ | 1 |
| 65A | —H | —H | —OCH₃ | —S—C₆H₄—C₆H₅ | 1 |
| 66 | —H | —H | —OCH₃ | —O—naphthyl | 1 |
| 66A | —H | —H | —OCH₃ | —S—naphthyl | 1 |
| 67 | —CH₃ | —H | —OCH₃ | —Cl | 1 |
| 68 | —H | —H | —OCH₃ | —O—CH₃ | 0 |
| 69 | —H | —CH₃ | —OCH₃ | —O—C₆H₅ | 0 |
| 70 | —H | —CH₃ | —OCH₃ | H₂C—C(CH₃)—O—CH—O (dioxolane) | 0 |

Column I

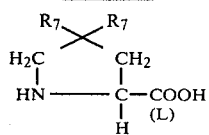

Column II

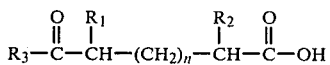

Column III

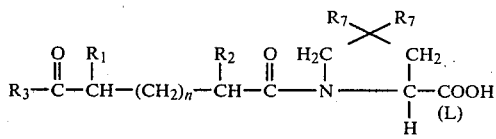

| Example | R₁ | R₂ | R₃ | R₇ | n |
|---|---|---|---|---|---|
| 71 | —H | | —CH₃ | —OCH₃ | (cyclohexane-1,3-dithio ring: H₂C-CH₂ / S-S) | 0 |
| 72 | —H | | —CH₃ | —OCH₃ | H₃C—CH—HC—CH₃ with S—S | |

In Examples 70–72, $R_7$ is $Y \rightarrow R_8$ where the $R_8$ groups join to complete an unsubstituted 5- or 6-membered ring or such ring wherein one or more carbon atoms are substituted by a lower alkyl or di(lower alkyl) group.

EXAMPLES 73–78

By following the procedure of Example 22 but using a proline of Column I in place of the cis-4-phenyl-thio-L-proline, of Example 22(b); and using the acid compound of Column II in place of the 3-methoxy-carbonyl-2-R-methylpropionic acid of Example 22(b) then the product of Column III is obtained.

Column I

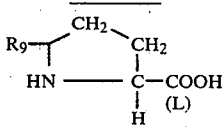

Column II

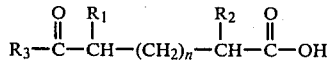

Column III

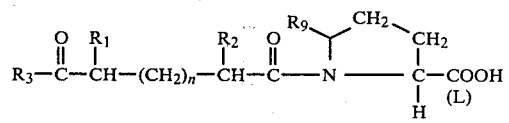

| Ex. | R₁ | R₂ | R₃ | R₉ | n |
|---|---|---|---|---|---|
| 73 | —CH₂—CH₂—⌬ | —H | —OCH₃ | =O | 1 |
| 74 | —H | —H | —OCH₃ | ⌬ | 0 |
| 75 | —H | —H | —OCH₃ | ⌬-OH | 1 |
| 76 | —H | —H | —OCH₃ | =O | 0 |
| 77 | —CH₃ | —H | —OCH₃ | ⌬ | 1 |
| 78 | —CH₃ | —CH₃ | —OCH₃ | ⌬ | 0 |

EXAMPLES 79–130

By following the procedure of Example 3(b) but using a product of Column III in Examples 27–78 in place of the 1-(3-methoxycarbonyl-2-methyl-propanoyl)-4,4-ethylenedithio-L-proline of Example 3(b), the corresponding free acid is obtained.

What is claimed is:

1. A compound of the formula

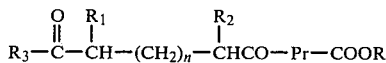

wherein

R is hydrogen or lower alkyl;

R₁ is hydrogen, lower alkyl or phenyl-lower alkyl;

R₂ is hydrogen, lower alkyl, phenyl-lower alkyl or halo substituted lower alkyl;

R₃ is hydroxy, —NHOH or lower alkoxy;

Pr—COOR is a substituted proline of the structure

![structures showing L-configuration amino acid derivatives with R4, R7, R9 substituents]

R$_4$ is halogen, keto, azido, cycloalkyl wherein cycloalkyl is a saturated ring of 3 to 7 carbons, phenyl, phenyl-lower alkyl, substituted phenyl or phenyl-lower alkyl wherein said substituent is on the phenyl ring and is selected from the group consisting of lower alkyl of 1 to 4 carbons, lower alkoxy of 1 to 4 carbons, lower alkylthio of 1 to 4 carbons, Cl, Br, F and hydroxy of said phenyl ring is di or trisubstituted with a substituent selected from the group consisting of methyl, methoxy, Cl and F, $$-O-\underset{\underset{O}{\|}}{C}-N\underset{R_5}{\overset{R_5}{\diagup}}$$

or Y-R$_6$;
R$_5$ is hydrogen or lower alkyl;
Y is oxygen or sulfur;
R$_6$ is lower alkyl, phenyl, phenyl-lower alkyl, substituted phenyl or phenyl-lower alkyl wherein said substituent is on the phenyl ring and is as defined above, a substituted or unsubstituted 1- or 2-naphthyl of the formula ![naphthyl with R14 substituents at positions 1,2]

or a substituted or unsubstituted biphenyl of the formula

![biphenyl with R14 substituents]

R$_7$ is halogen or —Y—R$_8$;
R$_8$ is lower alkyl, phenyl, phenyl-lower alkyl, substituted phenyl-lower alkyl wherein said substituent is on the phenyl ring and is as defined above, substituted or unsubstituted 1 or 2-naphthyl of the formula ![naphthyl with R14 substituents]

or substituted or unsubstituted biphenyl of the formula

![biphenyl with R14 substituents]

or the R$_8$ groups are lower alkyl which join to complete an unsubstituted 5- or 6-membered ring or such ring wherein one or more carbon atoms are substituted by a lower alkyl or di(lower alkyl) group;
R$_9$ is keto, phenyl, 2- or 4-hydroxyphenyl;
n is 0 or 1; and
R$_{14}$ is hydrogen, methyl, methoxy, methylthio, Cl, F, Br, or hydroxy; or a salt thereof.

2. A compound of claim 1 wherein
R is hydrogen or lower alkyl;
R$_1$ is hydrogen, lower alkyl or phenyl lower alkyl;
R$_2$ is hydrogen, lower alkyl, phenyl-lower alkyl or halo substituted lower alkyl;
R$_3$ is hydroxy, —NHOH or lower alkoxy;
R$_4$ is cyclohexyl, ![—(CH2)p—cyclohexyl with R14]

or Y—R$_6$;
R$_6$ is lower alkyl of 1 to 4 carbons,

![—(CH2)p—phenyl with R14]

a substituted or unsubstituted 1- or 2-naphthyl of the formula

![naphthyl with R14 substituents at positions 1,2]

a substituted or unsubstituted biphenyl of the formula

![biphenyl with R14 substituents]

p is zero, one or two;
R$_{14}$ is hydrogen, methyl, methoxy, methylthio, Cl, F, Br, or hydroxy;
R$_7$ is Cl, F or —Y—R$_8$;
Y is oxygen or sulfur;
R$_8$ is lower alkyl or the lower alkyl groups are joined to complete an unsubstituted 5- or 6-membered ring or said ring in which one or more of the carbons has a methyl or dimethyl substituent;

$R_9$ is phenyl, 2- or 4-hydroxyphenyl; and n is 0 or 1; or a salt thereof.

3. The compound of claim 2 wherein n is 0 or 1 and R is hydrogen.

4. The compound of claim 3 wherein $R_2$ is methyl, $R_1$ is hydrogen and n is zero.

5. The compound of claim 3 wherein $R_2$ is methyl, $R_1$ is phenylethyl and n is one.

6. The compound of claim 2 wherein Pr—COOR is

7. The compound of claim 6, 1-(3-carboxy-S-2-methylpropanoyl)-4,4-ethylenedioxy-L-proline.

8. The compound of claim 6, 1-(3-methoxycarbonyl-S-2-methylpropanoyl)4,4-ethylenedioxy-L-proline.

9. The compound of claim 2 wherein Pr—COOR is

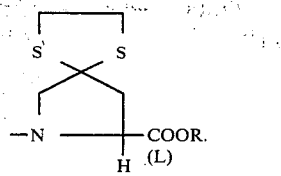

10. The compound of claim 9, 1-(3-carboxy-2-methylpropanoyl)-4,4-ethylenedithio-L-proline.

11. A composition for treating hypertension comprising an effective amount of a compound of claim 1 or a pharmaceutically acceptable salt thereof with a pharmaceutically acceptable carrier therefor.

12. The composition of claim 11 also including a diuretic.

13. The method of alleviating hypertension in mammals which comprises administering to a mammal an effective amount of the composition of claim 11.

* * * * *